(12) United States Patent
O'Rourke et al.

(10) Patent No.: US 6,292,610 B1
(45) Date of Patent: Sep. 18, 2001

(54) FIBER OPTIC PROBE AND COUPLER ASSEMBLY

(75) Inventors: Patrick E. O'Rourke, Martinez, GA (US); William R. Toole, Jr., Aiken, SC (US)

(73) Assignee: Equitech Int'l Corporation, Aiken, SC (US)

( * ) Notice: Subject to any disclaimer, the term of this patent is extended or adjusted under 35 U.S.C. 154(b) by 0 days.

(21) Appl. No.: 09/432,900

(22) Filed: Nov. 2, 1999

Related U.S. Application Data

(63) Continuation-in-part of application No. 09/031,521, filed on Feb. 27, 1998, now Pat. No. 5,978,534, which is a continuation-in-part of application No. 08/676,432, filed on Jul. 8, 1996, now Pat. No. 5,774,610.

(51) Int. Cl.[7] .............................. G02B 6/00; G02B 6/36
(52) U.S. Cl. .................................................. 385/52
(58) Field of Search ........................... 385/50–55, 147, 385/46, 44

(56) References Cited

U.S. PATENT DOCUMENTS

| | | |
|---|---|---|
| 3,190,735 | 6/1965 | Kapany . |
| 3,198,059 | 8/1965 | Phaneuf et al. . |
| 3,224,851 | 12/1965 | Hicks, Jr. . |
| 3,301,648 | 1/1967 | Sheldon . |
| 3,586,562 | 6/1971 | Jones . |
| 3,681,164 | 8/1972 | Bazinet, Jr. . |
| 3,917,383 * | 11/1975 | Cook et al. ............................ 385/54 |
| 4,165,014 * | 8/1979 | Villarruel et al. ..................... 385/52 |
| 4,173,392 | 11/1979 | Ekinaka et al. . |
| 4,212,512 * | 7/1980 | Hodgel ................................. 385/46 |
| 4,573,761 | 3/1986 | McLachlan et al. . |
| 4,923,268 | 5/1990 | Xu . |
| 5,058,985 | 10/1991 | Davenport et al. . |
| 5,185,832 | 2/1993 | Coutandin et al. . |
| 5,222,180 | 6/1993 | Kuder et al. . |
| 5,259,056 | 11/1993 | Davenport et al. . |
| 5,402,508 | 3/1995 | O'Rourke et al. . |
| 5,519,801 | 5/1996 | Le Noane et al. . |
| 5,710,626 | 1/1998 | O'Rourke et al. . |
| 5,774,610 | 6/1998 | O'Rourke et al. . |
| 5,978,534 * | 11/1999 | O'Rourke et al. ..................... 385/52 |

OTHER PUBLICATIONS

S. E. Nave, et al., "Sampling Probes Enhance Remote Chemical Analyses," *Laser Focus World*, Dec., 1995.

* cited by examiner

*Primary Examiner*—Akm E. Ullah
(74) *Attorney, Agent, or Firm*—Maria Reichmanis

(57) ABSTRACT

A fiber optic probe and optical coupler assembly, and methods for making the assembly and reproducibly aligning a plurality of optical fibers therein. The coupler is used with a probe that includes a housing or probe body, a probe tip, at least one light-transmitting fiber, at least one light-receiving fiber spaced apart from the light-transmitting fiber, and (if desired), in-line devices such as filters and lenses positioned in optical communication with the fibers. The coupler includes at least one aligning pin that helps maintain the transmitting and receiving fibers in precise, reproducible relative alignment therein; thus, the coupler can be cut to install filters and other in-line devices, then readily re-assembled for use with the cut ends precisely and accurately realigned. The coupler is simple and rugged, and can be manufactured and assembled without the need for high-precision machining or optical alignment procedures.

20 Claims, 6 Drawing Sheets

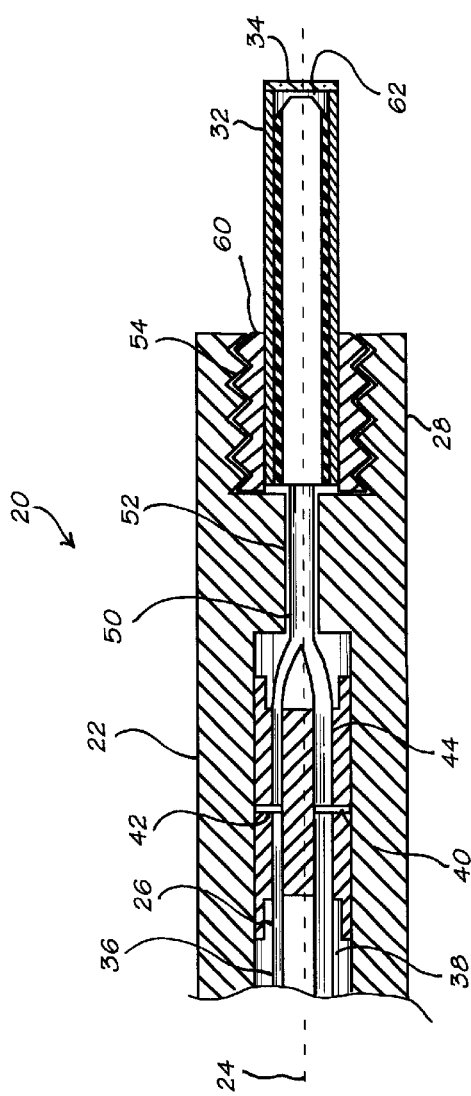
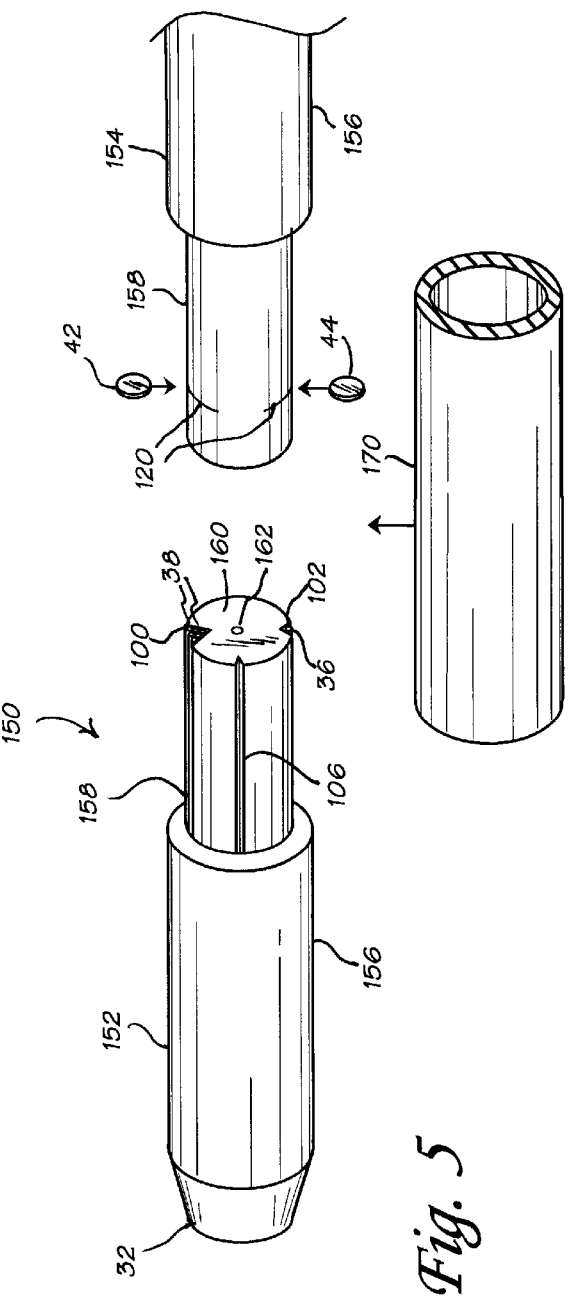
Fig. 1
Fig. 5

FIBER OPTIC PROBE AND COUPLER ASSEMBLY

This application is a continuation-in-part of application Ser. No. 08/676,432, filed Jul. 8, 1996, now U.S. Pat. No. 5,774,610, and application Ser. No. 09/031,521, filed Feb. 27, 1998 now U.S. Pat. No. 5,978,534.

BACKGROUND OF THE INVENTION

1. Field of the Invention

The present invention relates to fiber optic probes for spectrophotometry. In particular, the present invention relates to a rugged, mechanically stable coupler assembly for fiber optic probes, and to methods for making the assembly and aligning a plurality of optical fibers therein.

2. Discussion of Background

Recent developments in fiber optics, coupled with the availability of multichannel array-type spectrometers and multiplexing technology, have generated renewed interest in the use of remote spectroscopic techniques for in-line monitoring and process control, environmental monitoring, and medical applications. Signal transmission via optical fibers allows the placement of sensitive equipment in locations remote from industrial process streams, making remote sensing particularly attractive in harsh environments. Multiplexing—the capability of transmitting signals from a plurality of sources to a single instrument—facilitates the efficient use of complex and expensive instrumentation. Optical analysis techniques also improve the quality of the data. Data obtained from a sample is not always truly representative of the source of that sample, since the mere act of taking the sample can alter its properties; frequently, removing a sample can perturb the source as well. Optical analysis techniques can usually be undertaken without removing samples for laboratory analysis elsewhere; therefore, data from optical analyses is frequently more reliable than data obtained by other analytical techniques.

Remote fiber optic probes are essential for in-line monitoring and process control in corrosive and radioactive process environments. In the environmental field, fiber optic probes are used for in situ measurements of fluids in wells, boreholes, storage and process tanks, and so forth. Applications include monitoring groundwater flow, studying the migration of subsurface contaminants, evaluating the progress of remediation operations, and detecting toxic or explosive substances. Fiber optic probes can be used with absorption, diffuse reflectance, and Raman spectroscopy.

The absorbance of a substance is defined as $A=-\log_{10} T$, where $T=I/I_0$, I is the transmitted light intensity, and $I_0$ the incident light intensity. The absorption spectrum of a substance—the frequency distribution of the absorbance—is used to identify its composition; the amount of light absorbed at different frequencies depends on the concentration of each constituent. Spectrophotometry is the measurement of this absorption spectrum. A typical spectrophotometer includes these basic components: a light source, a probe containing light-transmitting and light-receiving fibers, and a detector. Light from the source is directed to the substance of interest by the transmitting fiber. The light is transmitted through the substance to the receiving fiber and the detector, which produces an output signal proportional to the absorbance of the substance over a range of frequencies. Measurements taken from a suitable reference sample are compared to measurements taken from the test sample to help determine the concentrations of various constituents in the test sample.

Absorption spectroscopy requires samples that are optically translucent or transparent in the range of frequencies being studied. Other techniques based on analysis of the light scattered by the sample, such as diffuse reflectance, fluorescence, and Raman spectroscopy, are useful for in situ analysis of solids or slurries (as used herein, the term "scattered light" includes both elastic (Rayleigh) scattering and inelastic (Raman and fluorescence) scattering). In probes designed for these types of measurements, light is directed to the sample through a transmitting fiber; scattered light is collected by the receiving fiber and returned to the detector. Probes designed for Raman spectroscopy can also be used for fluorescence. For purposes of the following discussion, the terms "Raman spectroscopy" "Raman spectrophotometry," and "Raman measurements" include all forms of inelastic scattering phenomena as well.

Raman spectrophotometry is a sensitive analytical technique based on the inelastic scattering of light (typically, monochromatic light from a laser) by an atom or molecule. While most of the scattered light has the same frequency as the incident light (Rayleigh scattering), a portion is frequency-shifted by an amount equal to one of the resonant frequencies of the molecule. Therefore, in addition to elastically-scattered light having the same frequency as the incident light, the scattered light contains small amounts of light with different frequencies. The pattern of frequency shifts is characteristic of the constituents of the sample; the intensity depends on the concentrations of each constituent in the sample. Raman spectrophotometry provides an excellent indicator, or fingerprint, of the types of molecules present in a sample.

Vibrational and rotational Raman spectra are typically in the visible or near infrared (NIR) region, therefore, Raman spectra are less severely attenuated than infrared (IR) absorption spectra by transmission over optical fibers. Therefore, Raman spectrophotometry can be done with normal silica fiber optic cables instead of the more expensive and fragile types of fibers needed for IR absorption spectrophotometry. In addition, Raman spectrophotometry is particularly useful for identifying the constituents of a substance since Raman spectra generally contain more spectral lines—and sharper lines—than other types of spectra.

A problem encountered in Raman spectrophotometry is the small scattering cross section, that is, the very low intensity of the Raman-scattered light compared to the intensity of the incident light (also termed the "exciting light"). Like absorption spectroscopy, Raman spectrophotometry requires a light source, an optical probe with light-transmitting and light-receiving fibers (also termed exciting and collecting fibers, respectively), and a detector. In addition to Raman-scattered light, some of the exciting light and some elastically-scattered light are reflected back to the receiving fiber. Light may also be reflected to the receiving fiber by the interior surfaces of the probe. In addition, monochromatic light transmitted by an optical fiber excites the fiber molecules, causing fluorescence and Raman scattering within the fiber itself. This "self-scattering" or "silica scattering" generates a signal that interferes with the Raman signal collected from the sample of interest.

When making Raman measurements with fiber optics, it is therefore necessary to reduce the amounts of nonshifted sample-induced scattered and reflected light returning to the spectrometer, as well as reduce fluorescence and silica Raman scattering generated in the fibers themselves. To filter out this noise, light from the transmitting fiber may be directed through a narrow bandpass filter at the fiber tip that transmits the laser frequency but rejects signals arising from the fiber (known as fluorescence and silica scattering) and extraneous light from the laser source (such as plasma lines, fluorescence, or superluminance). Light returning through the receiving fibers passes through a long-pass optical filter that rejects elastically-scattered light and reflected laser light but transmits Raman signals from the sample. High-intensity laser sources and sensitive detectors with high light gathering power and high stray light rejection are needed to isolate and measure the low intensity Raman signal due to the sample. Chemometric techniques are also used to help factor out background noise and identify the signal of interest. Instrumentation for Raman spectrophotometry is costly and delicate, requires high-precision, high-maintenance optical components, and is not well suited for use in many industrial process environments.

Presently-available fiber optic Raman probes include a probe having slanted tips (McLachlan, et al., U.S. Pat. No. 4,573,761). The transmitting fiber is surrounded by a plurality of receiving fibers spaced about the axis of a cylindrical housing which is closed at one end by a transparent window. The receiving fibers converge along lines which intersect at a point that is adjacent to or beyond the outer surface of the window. A Raman probe for light scattering measurements may include fibers with angled endfaces, such as the probe described in U.S. Pat. No. 5,402,508 issued to O'Rourke, et al., the disclosure of which is incorporated herein by reference. A variety of fiber optic probes, including Raman probes, are described by S. E. Nave, et al. in "Sampling probes enhance remote chemical analyses," Laser Focus World, December, 1995 (incorporated herein by reference). Several commercially available probes include efficient dual-fiber designs incorporating micro-optics, beamsplitters, and filters at the probe tip (such probes are available from Dilor Instruments SA (Edison, N.J.) and EIC Laboratories (Norwood, Mass.)).

A variety of closely packed multifiber arrays and processes for making such arrays are known in the art. Le Noane, et al. (U.S. Pat. No. 5,519,801) describe multicore optical guides wherein the optical fibers are very accurately positioned with respect to one another and with respect to the external contours of a matrix. Kuder, et al. (U.S. Pat. No. 5,222,180) place a bundle of polymer optical fibers into a rigid sleeve that has a softening point higher than the softening point of the fibers. When the resulting assembly is heated, the fibers expand, resulting in a close-packed geometry.

Ekinaka, et al. (U.S. Pat. No. 4,173,392) and Bazinet, Jr., et al. (U.S. Pat. No. 3,681,164) use bonding agents to hold a plurality of fibers in place. The Ekinaka, et al. glass fiber light guide consists of an elongated bundle of generally parallel glass fibers embedded in a hardened resin matrix, sheathed by a pair of thin protective layers. Bazinet, Jr., et al. apply a ceramic-based bonding agent to a bundle of fiber optic tips, then pull the bundle back into a plug until the tips are flush with the end.

Other methods for holding fibers in place include heat-shrinkable tubing and cords. Jones (U.S. Pat. No. 3,586,562), Hicks, Jr. (U.S. Pat. No. 3,224,851), and Phaneuf, et al. (U.S. Pat. No. 3,198,059) use heat shrinkable plastic tubing to secure the ends of a fiber bundle in place. Sheldon ties a cord about the ends of a bundle, then dips the ends in a cohesive liquid agent to permanently fix the ends in position (U.S. Pat. No. 3,301,648). The resulting bundle can be covered by heat-shrink tubing. Kapany makes a multifiber bundle by aligning a plurality of glass rods within a tube, then draws the resulting structure to the desired diameter (U.S. Pat. No. 3,190,735).

Multifiber couplers are used in many fiber optic devices. In U.S. Pat. Nos. 5,289,056 and 5,058,985, Davenport, et al. disclose an optical coupler that includes a housing and a plurality of optical fibers, the output ends of which are distributed to various spaced-apart locations. The input ends of the fibers are stripped of cladding, then compressed together within an inner sleeve so that boundaries between the individual ends are substantially eliminated. To protect the input ends from damage by high brightness light sources, a light-transmissive rod with a higher thermal coefficient than the fibers is disposed in optical contact with the input ends. Coutandin, et al. and Xu also use heat-shrinkable tubing in their devices. Coutandin, et al. (U.S. Pat. No. 5,185,832) make an optical coupler by bundling a plurality of polymer optical waveguides inside a plastic tube, pushing a heat-shrinkable sleeve over the tube, and heating to a temperature at which the sleeve contracts. Xu (U.S. Pat. No. 4,923,268) uses fibers that have a heat fusing temperature in a range achievable by exterior heating of a shrink sleeve. In his device, the fibers are fused together along a limited length within the sleeve. O'Rourke, et al. provide a Raman probe having a spring-loaded filter assembly, wherein the close proximity of the filter assembly to the probe tip minimizes self-scattering generated by the optical fibers (U.S. Pat. No. 5,710,626).

Presently-available Raman probes depend on precision optical components and single-strand optical fibers for excitation and light collection. Assembly of such probes requires high-precision machining and stringent optical alignment procedures. Conventional techniques for aligning the filters and optical fibers—and maintaining them in alignment—tend to be difficult and time-consuming to implement. The probes are expensive and delicate, rendering them unsuitable for most field installations. In part because of these problems, in part because other needed instruments were large, complex, and expensive, Raman spectrophotometry has historically been confined to research laboratories.

Our U.S. Pat. No. 5,774,610 and application Ser. No. 09/031,521, filed Feb. 27, 1998, the disclosures of which are incorporated herein by reference, describe fiber optic probe and optical coupler assemblies for light scattering measurements, and methods for making the assemblies and aligning a plurality of optical fibers therein. The probe includes a probe body with a window across its tip for protecting the interior, at least one light-transmitting fiber, at least one light-receiving fiber, and (if desired), in-line devices such as filters and lenses positioned in optical communication with the fibers. The coupler maintains the relative alignment of the fibers, which can be cut to install filters and other in-line devices. The design of the coupler allows the cut ends to be re-aligned quickly and accurately without the need for time-consuming procedures or costly precision alignment equipment. The probe is simple, rugged, requires no high-precision machining or optical alignment procedures in assembly, and is economical to manufacture.

Despite the availability of numerous designs for fiber optic probes, there is a continuing need for simple, rugged, inexpensive, easy-to-manufacture and easy-to-align probes for light scattering measurements (including but not limited to Raman measurements). The availability of a coupler that simplifies the alignment of light-transmitting and light-receiving fibers would further the use of Raman spectrophotometry and other optical techniques for on-line monitoring in a wide range of laboratory, medical, environmental, and industrial environments.

SUMMARY OF THE INVENTION

According to its major aspects and broadly stated, the present invention is an optical coupler assembly for use with fiber optic probes, and methods for making the assembly and precisely aligning a plurality of optical fibers therein. The coupler, which connects the transmitting and receiving fibers of a fiber optic probe or probe tip to an optical cable, is used with any suitable device that includes at least one light-transmitting fiber and at least one light-receiving fiber spaced apart from the transmitting fiber. If desired, the coupler may include in-line devices such as filters and lenses positioned in optical communication with the transmitting and receiving fibers. The coupler is simple, rugged, and economical to manufacture. Importantly, it allows for assembly of the probe without high-precision machining or optical alignment procedures.

In use, a probe that includes a coupler according to the invention is placed near a sample, with the transmitting fiber in optical communication with a light source and the receiving fiber in optical communication with a spectrophotometer. Light is directed to the sample by the transmitting fiber, where at least a portion of the light interacts with the sample to produce Raman-scattered light. Some of the scattered light is collected by the receiving fiber or fibers, and transmitted to a detector where the Raman spectrum of the sample is recorded and analyzed.

An important feature of the present invention is the two-part fiber optic coupler which maintains the relative axial alignment of the transmitting and receiving fibers. The coupler assembly carries at least one aligning pin (preferably at least two such pins), which is positioned so that the two portions of the coupler can be joined together in only one way, i.e. with the transmitting and receiving fibers correctly aligned. This is accomplished by forming suitably-positioned, longitudinal, spaced apart cavities in the body of the coupler, in the form of bores, peripheral notches, or a combination thereof. The cavities are dimensioned to hold corresponding aligning pins and configured so that the two portions of the coupler can be secured together with fibers correctly aligned. Here, "correctly aligned" means that the transmitting fiber (or fibers) of one portion is in optical communication with the transmitting fiber (or fibers) of the other portion; similarly, the receiving fiber(s) of one portion is in optical communication with the receiving fiber(s) of the other portion. While one aligning pin may be sufficient for purposes of carrying out the invention, two pins are preferred; three or more pins may also be useful. This feature permits precise, reproducible alignment of the transmitting and receiving optical fibers of the two coupler portions. As a result, in-line devices such as lenses, filters and the like can be installed (or replaced) as needed, as can other components of the probe, without the need for time-consuming precision alignment procedures.

Another feature of the present invention is the method for making the coupler with precisely-aligned optical fibers. The coupler is made using standard manufacturing techniques, simply by machining suitably-dimensioned cavities (peripheral notches, bores, etc.) approximately parallel to the longitudinal axis of the coupler. Transmitting and receiving fibers are installed in at least two of the cavities, fixed in place by epoxy or other suitable fixative. Then, the coupler is cut into two portions along a line approximately transverse to the longitudinal axis. Proper positioning of the cavities ensures that, when the aligning pins are correctly installed in their corresponding cavities in one of the two portions, the transmitting fibers and the receiving fibers of the two portions are automatically aligned correctly when the pins are plugged into the corresponding cavities in the other portion. If desired, in-line devices such as lenses and filters can be installed. For example, the cut fiber ends of one (or both) coupler portions could be coated with a suitable filter material.

Still another feature of the present invention is the aligning pin (or pins) used to align the two portions of the coupler. The pins may be of any convenient dimensions, and may have the same or different cross-sections. For example, the coupler may include two aligning pins, both having an approximately circular cross-section. Alternatively, the pins may have differently-shaped cross-sections (circular, square, hexagonal, etc.) and/or different dimensions to facilitate correct placement.

Still another feature of the present invention is the probe, which has a tip that, with the aid of the coupler, can quickly and easily be installed with the transmitting and receiving fibers precisely aligned with their counterparts in a probe body or optical cable. The tip may include a window to protect the optical fibers and other interior components of the probe from the samples being measured (and, in some cases, from harsh industrial process environments). The fibers themselves may have features such as slanted end-faces to maximize the collection of scattered light, thereby increasing the efficiency of the probe for applications where the light intensity is low.

Other features and advantages of the present invention will be apparent to those skilled in the art from a careful reading of the Detailed Description of a Preferred Embodiment presented below and accompanied by the drawings.

BRIEF DESCRIPTION OF THE DRAWINGS

In the drawings,

FIG. 1 is a cross-sectional view of a fiber optic Raman probe according to a preferred embodiment of the present invention;

FIG. 5 is a perspective view of another fiber optic coupler assembly according to the present invention;

DETAILED DESCRIPTION OF A PREFERRED EMBODIMENT

Figure 2A:
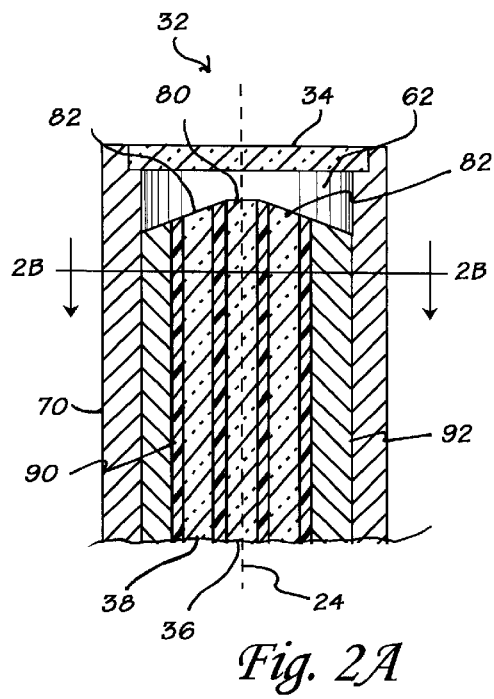
FIG. 2A is a detail view of the probe tip of FIG. 1.

In the following description, reference numerals are used to identify structural elements, portions of elements, or surfaces in the drawings, as such elements, portions or surfaces may be further described or explained by the entire written specification. For consistency, whenever the same numeral is used in different drawings, it indicates the same element, portion, surface and area as when first used. As used herein, the terms "horizontal," "vertical," "left," right," "up," "down," as well as adjectival and adverbial derivatives thereof, refer to the relative orientation of the illustrated structure as the particular drawing figure faces the reader.

Referring now to FIG. 1, there is shown a cross-sectional view of a fiber optic probe 20 according to a preferred embodiment of the present invention. Probe 20 includes a probe body 22 with a longitudinal axis 24, an interior 26, a proximal end 28, and a probe tip 32 with a window 34. At least one light-transmitting fiber 36, at least one light-receiving fiber 38, and a fiber optic coupler 40 are disposed in interior 26. In-line devices 42, 44 (lenses, filters, etc.) may be positioned in optical communication with fibers 36, 38, respectively, preferably inside coupler 40 generally as shown. Fibers 36, 38 are separate near distal end 28 and inside coupler 40; however, the fibers are joined into a single fiber bundle 50 inside probe tip 32. Bundle 50 holds fibers 36, 38 in a fixed arrangement, for example, a plurality of receiving fibers 38 surrounding a transmitting fiber 36. In use, transmitting fiber 36 is in optical communication with a light source such as a laser (not shown); receiving fiber 38 is in optical communication with a spectrophotometer (not shown).

Interior 26 of probe body 22 includes a narrow bore 52 and a distal portion 54, which may be threaded as shown in FIG. 1. If desired, springs (not shown) may be positioned in interior 25 about fibers 36, 38, at the proximal end of coupler 40 and between the distal end of coupler and bore 52. A fitting 60 is mounted at the proximal end of probe tip 32, threaded so that fitting 60 can be screwed into probe body 22. Alternatively, fitting 60 may be integrally formed with tip 32; if portion 54 is not threaded, tip 32 may be press-fitted into portion 54 and secured in position by any convenient means. Fitting 60, if present, is preferably of a type that maintains fiber bundle 50 in a fixed angular position relative to probe body 22. That is, bundle 50 does not rotate with respect to probe body 22 while fitting 60 is being screwed into or out of the body 22.

Probe body 22 and coupler 40 are preferably made of materials that are substantially impervious to the environment in which probe 20 is used, such as stainless steel. Other materials may also be useful, including brass, aluminum, and alloys such as Inconel. Window 34 is a thin window made of a transparent material such as sapphire, quartz, silica, polymers such as polystyrene, polycarbonate, Teflon® AF, or other suitable material, and is attached across the distal end of tip 34 so that a spacing 62 exists between the window and the distal end of fiber bundle 50. Window 34 is attached to probe tip 32 and positioned so as to avoid direct reflection from transmitting fiber 36 to receiving fibers 38. When window 34 is made of sapphire, the window is brazed into a metallic or ceramic tube (not shown) that provides a hermetically-sealed cover to protect the interior of probe tip 32. Other methods for attaching window 34 to the body of probe 20 may also be useful, depending on the material of the window and the anticipated uses of the probe. Depending on the choice of material for window 34, the thickness of the window, and the intended application of probe 20, the window may be substantially flat as shown, or curved.

Fibers 36, 38 are preferably single filament optical fibers with a transparent core, such as a fused silica core, enclosed in a cladding having a lower refractive index than the core. If desired, the fibers may be shielded by opaque jackets. The diameters of fibers 36, 38 are selected to optimize the collection of scattered light by receiving fibers 38. Fibers having core diameters of 300–600 microns are suitable for a broad range of applications; however, diameters outside this range may also be useful. When probe 20 is to be used in a radioactive environment, fibers 36, 38 are selected for good radiation resistance.

Figure 2B:
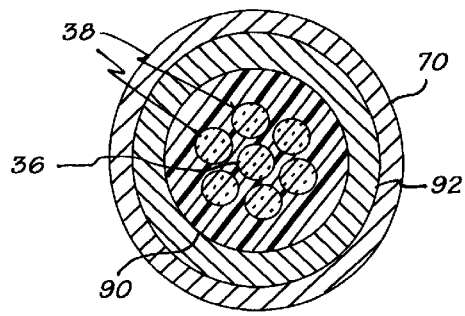
FIG. 2B is a cross-sectional view of the probe tip of FIG. 2A, taken along the lines 2B—2B of FIG. 2A.

Probe tip 32 is shown in detail in FIGS. 2A and 2B. Tip 32 includes a housing 70 with longitudinal axis 24, and contains at least one transmitting fiber 36 and at least one receiving fiber 38 (preferably, a plurality of receiving fibers 38 in a closely packed arrangement about the transmitting fiber). Fibers 36, 38 are oriented generally parallel to axis 24, thus, the fibers have optic axes parallel to axis 24. Transmitting fiber 36 has an endface 80 that is approximately perpendicular to axis 24 (and the optic axes of fibers 36, 38); receiving fibers 38 have endfaces 82 that are nonperpendicular to axis 24. As used herein, the term "endface" refers to the surface from which light enters or exits an optical fiber, that is, the surface at the cut end of the fiber. Endfaces 80, 92 may be shaped by cutting, grinding, polishing (to minimize imperfections on the cut surface) and like operations, preferably prior to attachment of tip 32 to probe body 22.

Fibers 36, 38 are held in position by a fixative 90 of epoxy or other suitable material. Fixative 90 is injected between fibers 36, 38 to maintain the spatial relationship and axial alignment of the fibers relative to housing 70 and each other. Probe tip 32 may also include a terminator 92. Fixative 90 adheres to the surfaces of fibers 36, 38, housing 70, and terminator 92 (if present) to hold the fibers securely within housing 70.

Figure 2C:
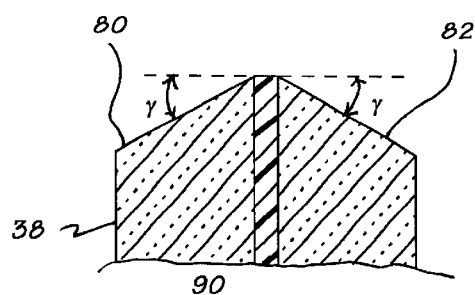
FIG. 2C is a detail view of the endfaces of two optical fibers of FIG. 2A, showing the bevel angle between the fibers.

Preferably, endfaces 80, 82 form a bevel having a bevel angle y selected to minimize direct reflection of light from transmitting fiber 36 to receiving fiber 38 (FIG. 2C). Bevel angle γ is preferably less than approximately 20° (the effects of direct reflection are more apparent at angles greater than 20°). To further reduce crosstalk between transmitting and receiving fibers 36, 38, fixative 90 is preferably spiked with a light absorber such as carbon black.

The optimum thickness of window 34 and the optimum separation between endfaces 80, 82 and the inner surface of the window depend on the type of samples to be measured with probe 20. Typically, window 34 is closer to endfaces 80, 82 for probes 20 used with solid or gaseous samples; thicker windows may be needed for probes used with liquid samples.

When probe 20 is used for Raman measurements, laser light from a source (not shown) is transmitted by fiber 36 and directed through window 34 to the sample. The light strikes the sample molecules, causing at least a portion of the light to be scattered, and, to some extent, directed towards receiving fibers 38. The light received by fibers 38 (including Raman-scattered light and non-Raman-scattered light) is transmitted by the fibers to a spectrometer system, where the data are recorded and analyzed to determine the composition of the sample.

Because the endfaces of the receiving fibers (fibers 38) are angled with respect to the endface of transmitting fiber 36, their cones of acceptance/transmission are refractively bent inward and cross the light cone of the central (i.e., transmitting) fiber at a common point near the tip of probe 20. This effect results in enhanced signals in opaque slurries or solids by factors of five to ten when compared to probes having flat tips.

Figure 3A:
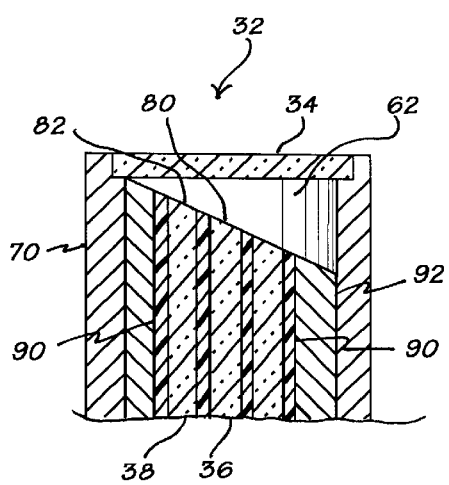
FIG. 3A is a detail, cross-sectional view of another probe tip usable with the invention.
Figure 3B:
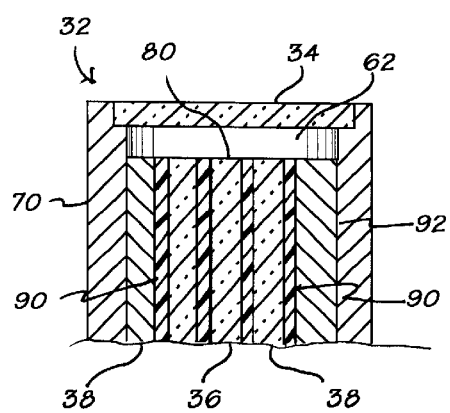
FIG. 3B is a detail, cross-sectional view of still another probe tip usable with the invention.

Other configurations of endfaces 80, 82 may also be useful in the practice of the invention. By way of example, endfaces 80, 82 may have a bevel angle of 0°, achieved by slanting the endfaces at the same angle (FIG. 3A), or cutting the endfaces substantially perpendicular to axis 24 (FIG. 3B).

Figure 4A:
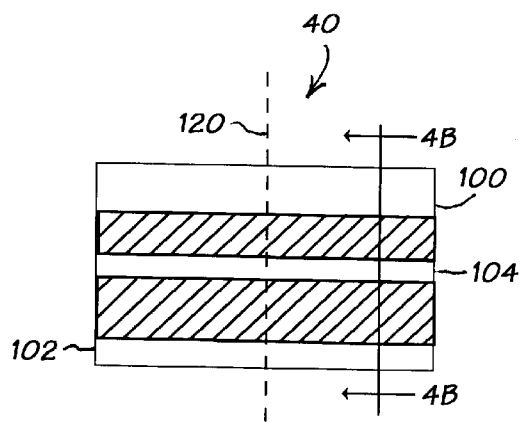
FIG. 4A is a detail, cross-sectional view of the fiber optic coupler assembly of FIG. 1.
Figure 4B:
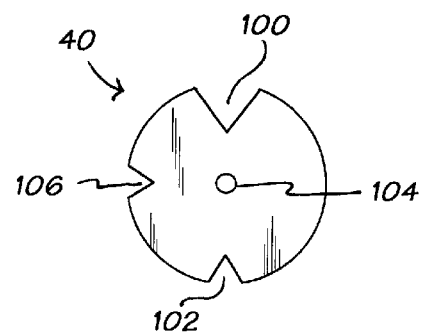
FIGS. 4B and 4C are end and perspective views, respectively, of the coupler assembly of FIG. 4A.

Referring now to FIG. 4A, there is shown a cross-sectional view of fiber optic coupler 40. Coupler 40 is a generally cylindrical body having at least one, and preferably at least three longitudinal cavities formed therein, one cavity for receiving an aligning pin and two for receiving light-transmitting and light-receiving fibers. For example, coupler 40 may have two spaced-apart longitudinal notches 100, 102 and a bore 104 extending through the body of the coupler. Notches 100, 102 and bore 104 are parallel to the longitudinal axis of coupler 40. Notches 100, 102 are dimensioned for holding optical fibers 36, 38, respectively, while bore 104 is dimensioned for an aligning pin to be described further below. Depending on the particular application, coupler 40 may be made of brass, aluminum, stainless steel, or some other metal or alloy. A cross-sectional view of coupler 40 is shown in FIG. 4B.

Notches 100, 102 may be formed by any suitable techniques, but are preferably machined in the body of coupler 40. Notches 100, 102 are dimensioned and configured according to the numbers of fibers 36, 38 to be installed therein, as well as the dimensions of the fibers: generally, a larger notch will accommodate a larger number of fibers. In typical applications, a plurality of light-receiving fibers 38 would be installed in a somewhat larger notch 100, and a single light-transmitting fiber 36 in a smaller notch 102.

Figure 4C:
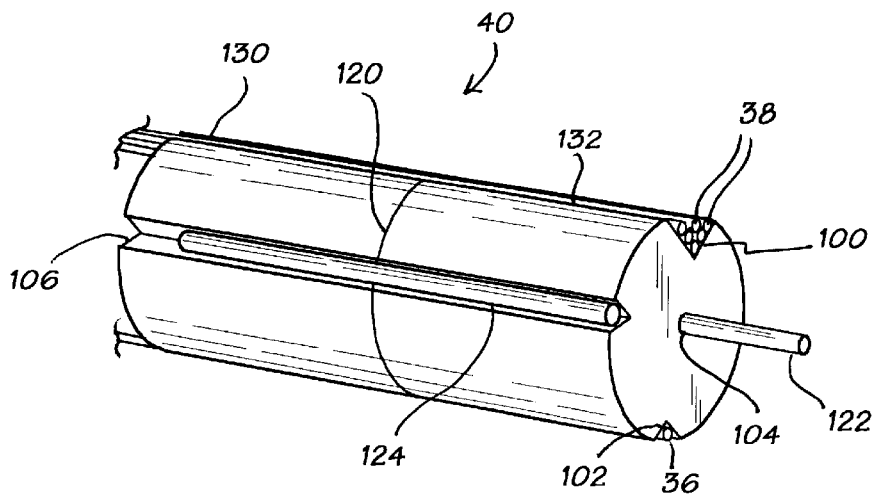

Optical fibers 36, 38 are then installed in notches 100, 102, and fixed in position by a suitable fixative (solder, epoxy, adhesive, and so forth). Each fiber is fixed over the entire length of its respective notch. If probe 20 is to include in-line devices 42, 44 (filters, lenses, etc.), at least one additional cavity such as alignment bore 104, and preferably another cavity such as a longitudinal notch 106 as well, are formed in the body of coupler 40 (FIGS. 4B, 4C). Then, coupler 40 is cut into two portions through a transverse line 120 which may extend partly or wholly through the coupler (FIGS. 4A, 4C), and the desired devices 42, 44 installed.

Devices 42, 44, if present, are any suitable optical devices that condition the light signal transmitted by fibers 36, 38, respectively. For example, device 42 may be a bandpass filter or laser pass filter that transmits the laser frequency but rejects other frequencies (including signals arising from transmitting fiber 36 (silica Raman and fluorescence) and extraneous light from the laser source (plasma lines, fluorescence, or superluminance)). Device 44 may be a laser rejection filter that rejects Rayleigh-scattered light and reflected laser light but transmits Raman signals from the sample. Devices 42, 44 may be thin filters or lenses that are inserted in-line as shown in FIG. 5 (see below); alternatively, filter material may be deposited onto the cut surfaces of fibers 36, 38 by sputtering, painting, dipping, or other convenient technique.

After installation of devices 42, 44, the opposing cut ends of coupler 40 are brought together and re-aligned by inserting alignment pins such as a pin 122 and a pin 124 (FIG. 4C) into bore 104 and notch 106. That is, after pins 122 and 124 are inserted into bore 104 and notch 106 of one of the two portions of coupler 40, that portion is positioned so that the pins are plugged into the corresponding bore 104 and notch 106 of the other portion. The cut ends of fibers 36, 38 are automatically correctly aligned in their original axial alignment. The cut ends of coupler 40 are brought together, and are then fixed in position by any convenient technique. Alignment pins 122, 124 may be removed if desired; alternatively, the pins may be left in place, fixed in position by epoxy, solder, or other suitable fixative.

Coupler 40 allows the easy installation of in-line filters and lenses without the need for time-consuming, high-precision optical alignment procedures. The original axial alignment of fibers 36, 38 with respect to each other is maintained simply by juxtaposing the cut ends of coupler 40 and adjusting the ends until pins 120 can be inserted through alignment holes 108, 110. The cut ends of each of fibers 36, 38 are then re-aligned essentially perfectly.

A fiber optic coupler 150 according to another preferred embodiment of the present invention is shown in FIG. 5. Coupler 150 includes two portions 152, 154, each having an outer housing 156 and a body 158 with a cut end 160 and a bore 162. Portion 152 may terminate in a probe tip such as above-described tip 32; portion 154 may be optically connected to a light source, a detector, and other instrumentation. The cut ends of transmitting fiber 36 and receiving fibers 38 are aligned with end 160 of portion 152 by butting body 158 (with fibers 36, 38 inserted therein in any desired arrangement) against a flat surface. Fibers 36, 38 are then fixed inside body 158 by epoxy or some other suitable fixative. The ends of matching fibers 36, 38 are similarly aligned inside tube 158 of portion 154. If desired, coupler 150 may be made in a single unit, then cut to form two portions 152, 154.

Devices 42, 44 are attached to some or all of fibers 36, 38, and portions 152, 154 connected to each other by means of a sleeve 170. Devices 42, 44 may be thin filters or lenses (such as device 42 shown in FIG. 5); alternatively, a suitable filter material may be deposited onto the surfaces of fibers 36, 38.

To assemble coupler 150, sleeve 170 is slipped over one of ends 160, then, the other end is inserted into the sleeve. When the two ends 160 are juxtaposed, their respective fibers 36 are aligned. Fibers 38 may be aligned by shining light down any one of fibers 38 of either of portions 152, 154, and rotating one of the portions to determine the angular position at which the transmitted light is maximized. At this position, all of fibers 36, 38 are correctly aligned.

Body 158 may, of course, be replaced by above-described coupler 40. If desired, housing 156 may be threaded so that the housing can be quickly screwed onto body 158; alternatively, the cut ends of body 158 may be externally threaded, and the ends of sleeve 170, internally threaded, so that the parts of probe 150 can be easily assembled or disassembled. This construction facilitates replacement of a probe tip during operation of any instrumentation that makes use of a probe according to the present invention.

Figure 6:
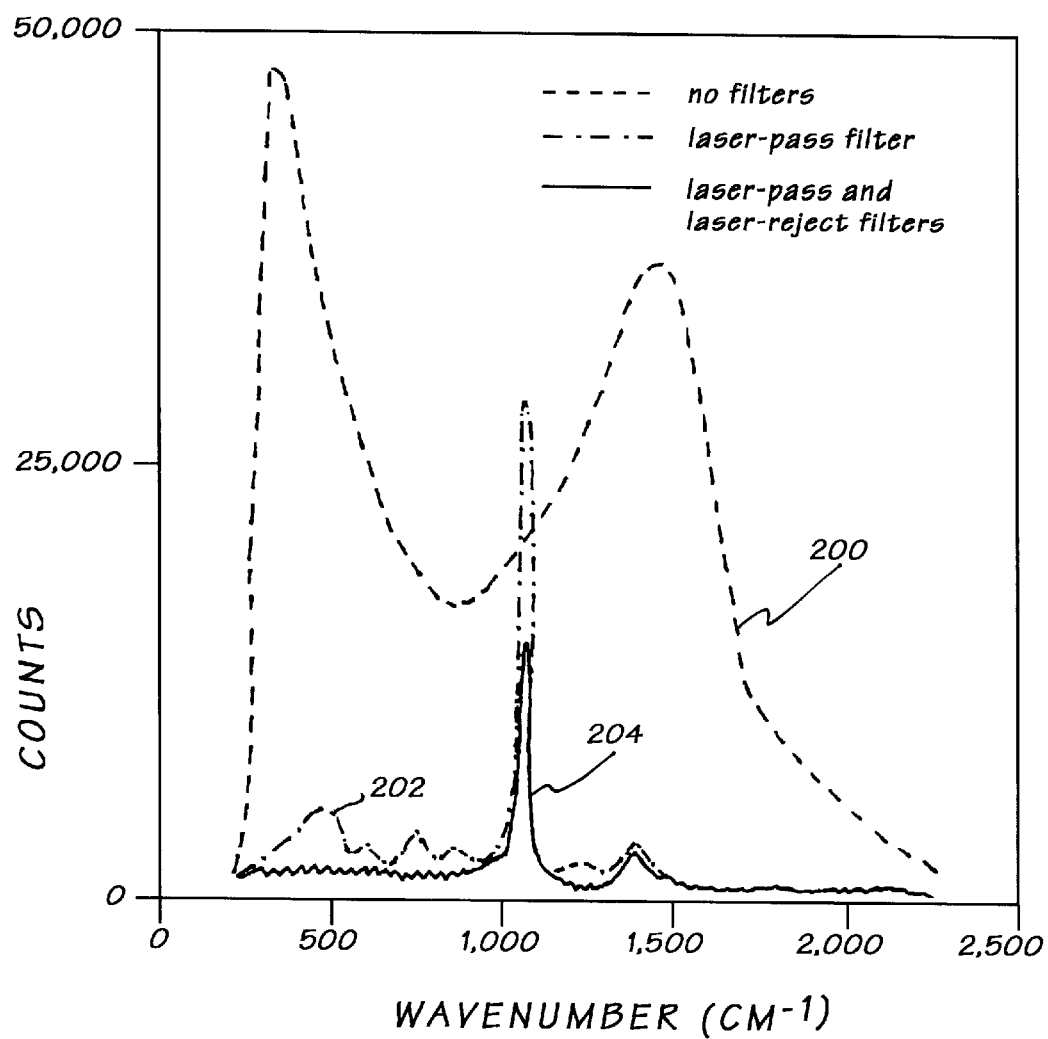
FIG. 6 shows the Raman spectrum of sodium nitrate.

An example of the type of data enhancement that is achievable with a proper choice of in-line filters (i.e., devices 42, 44) is shown in FIG. 6. The Raman spectrum of sodium nitrate powder was obtained without filters (spectrum 200), with a laser pass filter only (spectrum 202), and with laser-pass and laser-reject filters (spectrum 204). In-line filters produced sharper spectra; the greatest improvement was with both pass and reject filters (204).

Figure 7:
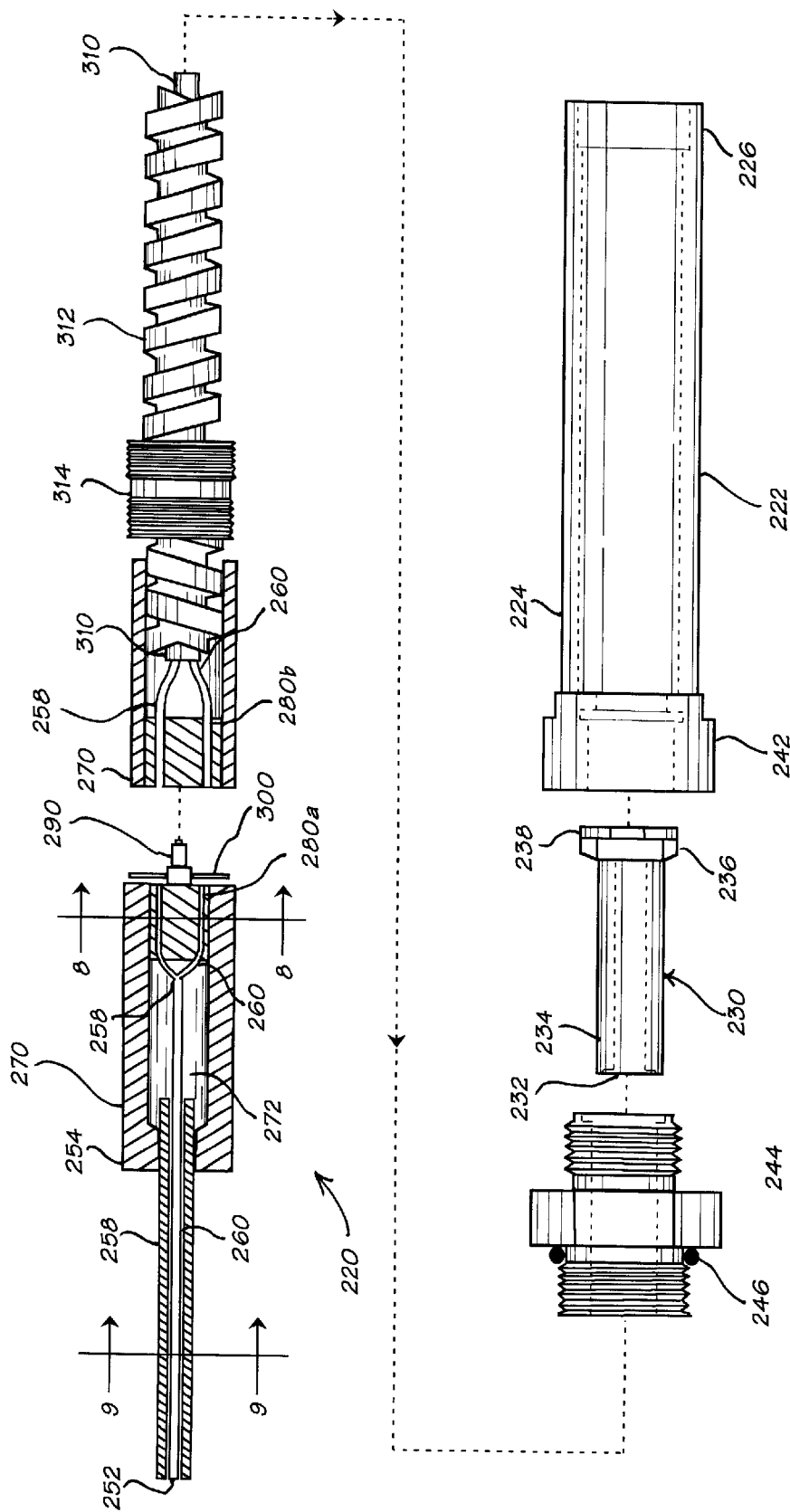
FIG. 7 is a partially-exploded, cross-sectional view of another fiber optic Raman probe according to the present invention.

Referring now to FIG. 7, there is shown another fiber optic Raman probe 220 according to a preferred embodiment of the present invention. Probe 220 has a cylindrical outer housing 222 with a distal end 224 and a proximal end 226, made from stainless steel, aluminum, or other suitable metal or alloy. For example, outer housing 222 may be made of Type 316 stainless steel tubing, with a 0.5" outside diameter and 0.375" inside diameter. Of course, other materials and dimensions may also be useful.

Preferably, all exposed parts of probe 220, including housing 222, are compatible with the environment of use of the probe. Both distal end 224 and proximal end 226 are threaded at both ends. Depending on the type of connectors to be used with the housing, ends 224, 226 may be internally-threaded or externally threaded.

A generally tubular connector 230 is installed at distal end 224. Connector 230 is made of high purity alumina, and has a window 232 at its distal end 234. A ferrule 236, of graphite, Teflon™ or other suitable material, together with a washer 2338, are installed at a proximal end 240, held in place by a nut 242, such as a lock nut or a compression fitting back nut. A connector 244 and an O-ring 246 are installed on distal end 232 of connector 230.

Probe 220 has an tip 250 of any convenient length. Tip 250 has a forward, distal end 252, a proximal end 254, and a tubular housing 256 (of stainless steel, aluminum, or other suitable material). Tip 250 holds at least one light-transmitting fiber 258 for transmitting light from a source such as a laser, and at least one light-receiving fiber 260 that receives scattered light and transmits the light back to a detector. Receiving fiber 260 is preferably a fiber bundle that contains a plurality of optical fibers.

Fibers 36, 38, 258, 260 may be silica core fiber optic cables with doped silica cladding having a low OH⁻ and a polyimide buffer. However, for applications where a low signal-to-noise ratio is desired, non-silica fibers such as zirconium fluoride fibers are preferred, at least for transmitting fibers 38, 260. Non-silica fibers have a lower Raman cross-section than silica fibers in certain regions of the spectrum, thus, a lower silica background signal and a correspondingly higher signal-to-noise ratio.

Figure 9:
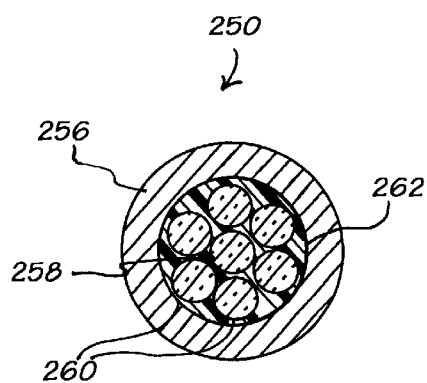
FIG. 9 is a cross-sectional view of the probe tip of FIG. 7, taken along the lines 9—9 of FIG. 7.

In a preferred embodiment of the invention, fiber 258 is a single optical fiber, and fibers 260 are a bundle of six optical fibers arranged as shown in FIG. 9. Fibers 258, 260 are affixed in a tightly packed bundle arrangement within housing 256 by an epoxy matrix 262. If desired, matrix 262 may be a carbon-black filled epoxy that helps minimize cross-talk between the fibers. Tip 252 preferably has slanted endfaces as shown in above-described FIGS. 1, 2A, and 3A; however, other configurations may also be useful. Depending on the environment of use of probe 220, tip 252 may include a window such as window 34 (FIG. 2A). Window 34, if present, is made of sapphire, quartz, or other suitable material, preferably affixed to tip 252 by brazing.

Figure 8:
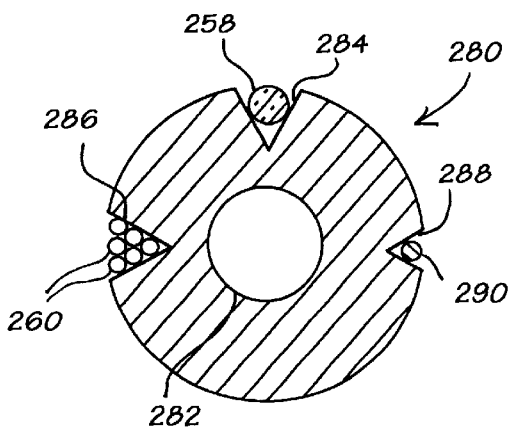
FIG. 8 is a cross-sectional view of the coupler assembly of FIG. 7, taken along the lines 8—8 of FIG. 7.

Proximal end 254 of tip 250 terminates in an inner housing 270 having an interior 272 with a fiber optic coupler assembly 280 (FIG. 8). Tubular coupler 280 has a central bore 282 and three spaced-apart longitudinal notches 284, 286, 288 formed therein. Notches 284, 286 are dimensioned for optical fibers 258, 260, respectively; notch 288 holds an aligning pin 290. Coupler 280 and pin 290 may be made of stainless steel, aluminum, brass, or indeed any metal or alloy suitable for the particular application.

Notches 284, 286 are dimensioned according to the numbers of fibers 258, 260 to be installed therein, as well as the dimensions of the fibers. In a preferred embodiment, a single transmitting fiber 258 is installed in notch 284, and a plurality of receiving fibers 260 are installed in a somewhat larger notch 286.

Fibers 258, 260 are installed into notches 284, 286 generally as shown in FIG. 8, and fixed in position by a suitable fixative (solder, epoxy, adhesive, and so forth). Each fiber is fixed over the entire length of its respective notch. Then, coupler 280 is cut into two portions 280a, 280b (FIG. 7).

If desired, in-line devices such as lenses or filters 300 can be installed as indicated in FIG. 7. Devices 300, if present, are any suitable optical devices that condition the light signal transmitted by fibers 258, 260. For example, device 300 may be a bandpass filter or laser pass filter that transmits the laser frequency but rejects other frequencies (including signals arising from transmitting fiber 258 and extraneous light from the laser source (plasma lines, fluorescence, or superluminance)). Device 300 may be a laser rejection filter that rejects Rayleigh-scattered light and reflected laser light but transmits Raman signals from the sample. Alternatively, filter material may be deposited onto the cut surfaces of fibers 258, 260 by sputtering, painting, dipping, or other convenient technique.

After installation of devices 300 (if present), the opposing cut ends of coupler 280 are brought together and re-aligned by aligning notches 284, 286 with fibers 258, 260, respectively, and inserting an alignment pin 290 into notch 288 (FIG. 8). The cut ends are maintained in position by alignment pin 290 and outer housing 222 (FIG. 7).

Coupler 280 allows the easy installation and removal of probe tip 250 from probe 220, in addition to installation and removal of in-line filters and lenses without the need for time-consuming, high-precision optical alignment procedures. The original axial alignment of fibers 258, 260 with respect to each other is maintained simply by juxtaposing the cut ends of coupler 280 so that their respective notches 284, 286 are aligned with alignment pin 290 in notch 288. The cut ends of each of fibers 258, 260 can be re-aligned reliably and reproducibly.

The proximal ends of fibers 258, 260 are encased in a sheath 310 (of Teflon™ or other suitable material) and, preferably, in a flexible armor casing 312. Casing 132 is attached to inner housing 270 and outer housing 222 by a back nut 314. Sheath 310 with fibers 258, 260 are free to piston inside casing 312 (i.e., to move longitudinally backwards and forwards, to some degree, inside the casing). Thus, the casing not only helps protect fibers 258, 260 from the environment, but also provides strain relief to minimize fiber deterioration and breakage due to bending, crimping, and the like.

All materials used for probe 220 are selected with a view to the anticipated use of the probe. For example, materials that can withstand high temperatures (on the order of 300° C. or higher), including high-temperature epoxy, Teflon™ tubing, and so forth are preferred for many process environments. Casing 144 may be made of any suitable metal or alloy; casings made of aramid fiber materials such as Kevlar™ may also be useful.

Figure 10A:
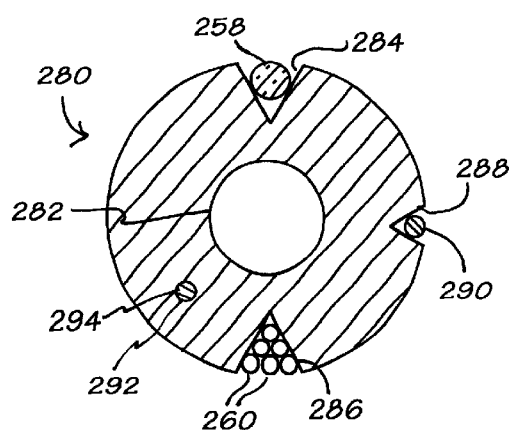
FIGS. 10A–10C are cross-sectional views of additional coupler assemblies usable with the invention.
Figure 10B:
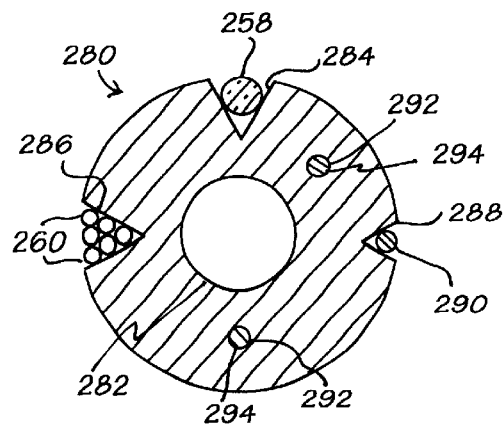
Figure 10C:
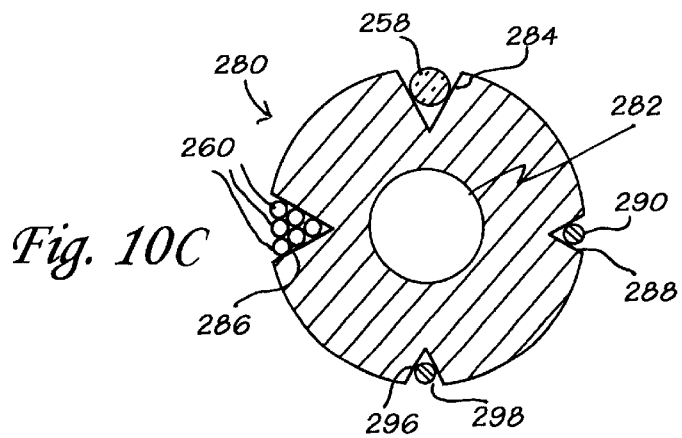

Coupler 280 may have additional configurations within the spirit of the present invention. By way of example, coupler 280 may have a second alignment pin 292 in a bore 292 (FIG. 10A), two alignment pins 292 in spaced-apart bores 294 (FIG. 10B), or two pins 290, 296 in two notches 288, 298 (FIG. 10C). For operability and easy alignment of fibers 258, 260, coupler 280 has notches 284, 286 for fibers 258, 260, respectively, and at least notch or bore for insertion of an aligning pin. These must be positioned so that there is only one correct way to position coupler portions 280a, 280b with respect to each other: with the cut ends of fibers 258, 260 optically aligned with each other. Thus, notches 258, 260 and notch 288 (or the other alignment configurations usable with the invention) must be asymmetrically positioned when viewed in cross-section. Some useful configurations of this type are shown in FIGS. 8 and 10A–C.

Probe tip 250 and coupler 280 may be manufactured generally as follows: Fibers 258, 260 are fitted into a tube of any suitable dimensions (housing 256), such as a stainless steel tube having an outer diameter of 0.120", an inner diameter of 0.056", and any convenient length (for example, approximately 1"–2"). The polyimide cladding is removed from the ends of the fibers, which are then dipped into high-temperature epoxy and drawn back into the tube leaving approximately 1/16" exposed.

Coupler 280 is made by cutting a 3/8" diameter metal rod to approximately 1.5" length, drilling a 0.25" diameter hole almost through the length of the rod to form outer housing 270. Then, a 60° V-groove is milled to a depth of approximately 0.02" into a 0.25" diameter, 1.25" long aluminum standoff to form notch 288. The standoff is rotated approximately 90°, and a second V-groove is milled to a depth of about 0.05" to form notch 284. The standoff is rotated yet again, and milled to a depth of 0.05" to form notch 286. Transmitting fiber 258 is installed into notch 284, receiving fibers 260 into notch 286, and the assembly is installed into outer housing 270. The polyimide coating is removed from the fiber tips, then the fibers are fixed with high-temperature. After the epoxy has cured, the resulting assembly is cut to form coupler sections 280a, 280b. Alignment pin 290 is placed in notch 288.

Notches 258, 260, 288 of coupler 280 may have approximately V-shaped cross-sections as shown; notches 100, 102, 106 may also be approximately V-shaped. However, it will be evident that the notches may have any other convenient shape, including rounded, partial-circular, and angular cross-sections.

A fiber optic coupler according to the present invention is simple, rugged, and has a minimum of components. The coupler is also economical to manufacture, since high-precision machining techniques and optical alignment procedures are not needed. Couplers 40, 150, and 280 allow for the straightforward installation and removal of probe tip 250, and, if desired, other devices such as in-line filters, without the need for additional optical connectors. Importantly, the transmitting and receiving fibers of a probe that includes the coupler can be aligned reliably and reproducibly, without complex and time-consuming optical alignment techniques. Thus, probe tip 250 can easily be removed or replaced during routine servicing, or replaced with another type of probe tip to accommodate changed conditions or different measurement needs. Furthermore, couplers 40, 150, 280 can be manufactured by standard precision machining techniques, so that the invention is economical to manufacture. The particular components of probes 20, 220, including the configuration of probe tip 250, depend on the types of samples to be measured and the anticipated environment of use.

It will be apparent to those skilled in the art that many changes and substitutions can be made to the preferred embodiment herein described without departing from the spirit and scope of the present invention as defined by the appended claims.

What is claimed is:

1. A fiber optic coupler assembly, said coupler assembly comprising:
  a first body portion having formed therein means for receiving at least one first optical fiber and means for receiving at least one second optical fiber;
  a second body portion having formed therein means for receiving at least one first optical fiber and means for receiving at least one second optical fiber; and
  means for aligning said first and second body portions so that said first optical fiber of said first body portion is in optical communication with said first optical fiber of said second body portion, and said second optical fiber of said first body portion is in optical communication with said second optical fiber of said second body portion.

2. The coupler assembly as recited in claim 1, wherein said first body portion further comprises a first generally cylindrical body having two spaced-apart longitudinal notches formed therein, one of said notches dimensioned for holding said at least one first optical fiber of said first body portion and the other of said notches dimensioned for holding said at least one second optical fiber of said first body portion, and wherein said second body portion further comprises a second generally cylindrical body having two spaced-apart longitudinal notches formed therein, one of said notches dimensioned for holding said at least one first optical fiber of said second body portion and the other of said notches dimensioned for holding said at least one second optical fiber of said second body portion.

3. The coupler assembly as recited in claim 1, wherein said first body portion has at least two longitudinal bores therethrough, one of said bores dimensioned for holding said at least one first optical fiber of said first body portion and another of said bores dimensioned for holding said at least one second optical fiber of said first body portion, and wherein said second body portion has at least two longitudinal bores therethrough, one of said bores dimensioned for holding said at least one first optical fiber of said second body portion and another of said bores dimensioned for holding said at least one second optical fiber of said second body portion.

4. The coupler assembly as recited in claim 1, further comprising means for holding said first and second optical fibers of said first body portion in optical communication with a probe tip.

5. The coupler assembly as recited in claim 1, further comprising an optical device in optical communication with at least one of said at least one first optical fiber of said first body portion and said at least one first optical fiber of said second body portion.

6. The coupler assembly as recited in claim 1, further comprising an optical device in optical communication with at least one of said at least one second optical fiber of said first body portion and said at least one second optical fiber of said second body portion.

7. A fiber optic coupler assembly, said coupler assembly comprising:
  a first generally cylindrical body;
  at least one first light-transmitting fiber installed in said first body;
  at least one first light-receiving fiber installed in said first body;
  a second generally cylindrical body;
  at least one second light-transmitting fiber installed in said second body;
  at least one second light-receiving fiber installed in said second body; and
  means for aligning said first and second body portions so that said first light-transmitting fiber is in optical communication with said second light-transmitting fiber and said first light-receiving fiber is in optical communication with said second light-receiving fiber.

8. The coupler assembly as recited in claim 7, wherein said aligning means further comprises at least one cavity formed in said first body portion and at least one corresponding cavity formed in said second body portion.

9. The coupler assembly as recited in claim 7, wherein said first body has two spaced-apart longitudinal notches formed therein, one of said notches dimensioned for holding said at least one first light-transmitting fiber and the other of said notches dimensioned for holding said at least one first light-receiving fiber, and wherein said second body has two spaced-apart longitudinal notches formed therein, one of said notches dimensioned for holding said at least one second light-transmitting fiber and the other of said notches dimensioned for holding said at least one second light-receiving fiber.

10. The coupler assembly as recited in claim 7, wherein said first body has two longitudinal bores formed therein, one of said bores dimensioned for holding said at least one first light-transmitting fiber and the other of said bores dimensioned for holding said at least one first light-receiving fiber, and wherein said second body has two longitudinal bores formed therein, one of said bores dimensioned for holding said at least one second light-transmitting fiber and the other of said bores dimensioned for holding said at least one second light-receiving fiber.

11. The coupler assembly as recited in claim 7, further comprising means for holding said first light-transmitting and first light-receiving fibers in optical communication with a probe tip.

12. The coupler assembly as recited in claim 7, further comprising means for holding said second light-transmitting and second light-receiving fibers in optical communication with a probe body.

13. The coupler assembly as recited in claim 7, further comprising an optical device in optical communication with at least one of said first light-transmitting fiber and said second light-transmitting fiber.

14. The coupler assembly as recited in claim 7, further comprising an optical device in optical communication with at least one of said first light-receiving fiber and said second light-receiving fiber.

15. The coupler assembly as recited in claim 7, wherein said coupler includes at least one non-silica fiber.

16. The coupler assembly as recited in claim 7, wherein each of said first and second bodies has a longitudinal axis and at least one bore therethrough, said bore being approximately parallel to said longitudinal axis of said assembly, and wherein said aligning means further comprises an aligning pin dimensioned to just fit in said at least one bore.

17. A method for making an optical coupler, said method comprising the steps of:

installing at least one light-transmitting fiber in a generally cylindrical body, said body having a longitudinal axis;

installing at least one light-receiving fiber in said body;

providing at least one alignment means in said body, said at least one light-transmitting fiber and said at least one light-receiving fiber being approximately parallel to said longitudinal axis; and cutting said body into two portions along a line approximately transverse to said longitudinal axis so that said two portions can be realigned with said light-transmitting fiber of one portion in optical communication with said light-transmitting fiber of the other portion, and said light-receiving fiber of said one portion in optical communication with said light-receiving fiber of said other portion.

18. The method as recited in claim 17, further comprising the step of forming two longitudinal cavities through said body, said cavities being approximately parallel to said longitudinal axis, one of said cavities dimensioned for receiving said at least one light-transmitting fiber and the other of said cavities dimensioned for receiving said at least one light-receiving fiber.

19. The method as recited in claim 17, wherein said providing step further comprises forming at least one cavity through said body, said at least one cavity dimensioned for receiving an aligning pin.

20. The method as recited in claim 17, further comprising the step of installing at least one optical device in optical communication with at least one of said light-transmitting and said light-receiving fibers.

* * * * *